United States Patent
Franzke et al.

(12) 
(10) Patent No.: US 6,214,319 B1
(45) Date of Patent: *Apr. 10, 2001

(54) AQUEOUS-ALCOHOLIC HAIR FIXING COMPOSITION CONTAINING A COMBINATION OF SHELLAC AND SYNTHETIC HAIR FIXING POLYMER

(75) Inventors: Michael Franzke, Rossdorf; Harald Wendel, Ober-Ramstadt; Jürgen Schmenger, Weiterstadt, all of (DE)

(73) Assignee: Wella Aktiengesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/956,063

(22) Filed: Oct. 22, 1997

(30) Foreign Application Priority Data

Nov. 7, 1996 (DE) .............................. 196 45 909

(51) Int. Cl.[7] ........................................ A61K 7/11
(52) U.S. Cl. .......................... 424/47; 424/45; 424/70.11; 424/70.13; 424/70.14; 424/70.16; 424/70.17; 424/70.21; 424/DIG. 1; 424/DIG. 2
(58) Field of Search .................... 424/45, 47, DIG. 1, 424/DIG. 2, 70.11, 70.13, 70.14, 70.15, 70.16, 70.17, 70.21

(56) References Cited

U.S. PATENT DOCUMENTS 5,053,218 10/1991 Shernov .
5,304,368 4/1994 Shernov .

FOREIGN PATENT DOCUMENTS

| 283 604 | 8/1970 | (CH) . |
|---|---|---|
| 44 22 593 | 1/1996 | (DE) . |
| 0 551 748 | 7/1993 | (EP) . |
| 1 296 021 | 11/1972 | (GB) . |
| 94 08554 | 4/1994 | (WO) . |
| 96 00565 | 1/1996 | (WO) . |

OTHER PUBLICATIONS

E. L. Roehl "Grundstoffe Haarpflegemittel Mit Festlegender Wirkung", Dragoco Report 7 (1962), s. 153–170.

*Primary Examiner*—Raj Bawa
(74) *Attorney, Agent, or Firm*—Michael J. Striker

(57) ABSTRACT

The aqueous-alcoholic hair fixing composition contains from 0.1 to 10 percent by weight of shellac, neutralized from 50 to 100%; from 0.01 to 20 percent by weight of at least one film-forming hair fixing synthetic polymer, advantageously a terpolymer made from octylacrylamide, t-butylaminoethylmethacrylate and at least two monomers selected from the group consisting of methacrylic acid, esters of acrylic acid and esters of methacrylic acid; from 30 to 70 percent by weight of at least one alcohol containing from 1 to 4 carbon atoms; from 30 to 70 percent by weight water; and, for compositions to be sprayed by means of a propellant, from 15 to 85% by weight of a propellant, advantageously dimethylether, an alkane, $N_2$, $N_2O$ or $CO_2$. The combination of the shellac and the synthetic hair fixing polymer causes a synergistic viscosity lowering which advantageously promotes rinsibility without impairing fixing performance.

9 Claims, No Drawings

AQUEOUS-ALCOHOLIC HAIR FIXING COMPOSITION CONTAINING A COMBINATION OF SHELLAC AND SYNTHETIC HAIR FIXING POLYMER

BACKGROUND OF THE INVENTION

The present invention relates to an aqueous-alcoholic composition for fixing hair with a content of neutralizable shellac in combination with at least one additional film-forming hair fixing polymer.

Conventional compositions for fixing hair, especially hair sprays, employ lower alcohols, such as ethanol or isopropanol as solvents for the film-forming, hair fixing ingredients. These lower alcohols are volatile organic compounds (VOC), which have been mentioned as contributors to air pollution. Thus because of environmental considerations, it is desirable to try to find hair fixing compositions which have reduced amounts of volatile organic solvents. This can occur by replacing all or part of the lower alcohols with water. Aqueous alcohol-free hair sprays are, of course, known, but they have disadvantageous properties during use, especially in regard to the required lengthy drying time.

Compositions for fixing hair, in which a part of the lower alcohol is replaced by water, are similarly known. This type of aqueous-alcoholic system has the disadvantage that it is difficult to spray, since alcohol/water mixtures with an alcohol content of between 30 and 60 percent have a viscosity maximum. This viscosity maximum occurs in an even greater extent in the presence of conventional hair-fixing polymers

SUMMARY OF THE INVENTION

It is an object of the present invention to provide a composition for fixing hair, which has a reduced portion of volatile organic solvents, may be satisfactorily sprayed and simultaneously has good application properties.

It has been found that a viscosity lowering of aqueous-alcoholic solutions is caused by addition of shellac to the commercially available film-forming polymers, which causes an extraordinarily advantageous effect on the rinsability properties of these aqueous-alcoholic systems. By measurement of the force required for breaking of the film formed on the hair(breaking force measurement), it was found that the fixing properties of the composition of the invention were not significantly changed by partial replacement of the polymer with shellac.

The composition of the invention for hair treatment comprises
  (A) shellac which is from 50 to 100% neutralized;
  (B) at least one film-forming hair fixing synthetic polymer;
  (C) from 10 to 80 percent by weight, preferably from 30 to 70 percent by weight, for at least one alcohol containing from 1 to 4 carbon atoms; and
  (D) from 20 to 90 percent by weight, preferably from 30 to 70 percent by weight, water.

The ingredient A of the composition according to the invention is preferably used in the hair treatment composition according to the invention in a concentration of from 0.1 to 10 percent by weight, preferably in a concentration of from 0.5 to 5 percent by weight. A suitable product is, for example, marketed under the trade name Schellack MHP 210 of Pennig, Hamburg, Germany, or in pre-neutralized form with borax under the trade name, Spezialschellack SSB 63 HE-N of Stroever, Germany.

The neutralization agent for the shellac can, for example, be a primary, secondary or tertiary amine, aminoalcohol, alkali hydroxide or ammonia in the form of an aqueous ammonia solution. Preferred neutralization agents include 2-amino-2-methylpropanol, triisopropylamine, sodium hydroxide and aqueous ammonia solution.

Ingredient B of the hair treatment composition according to the invention is preferably used in a concentration of from 0.01 to 20 percent by weight, especially preferably in a concentration of from 0.1 to 10 percent by weight. By "film-forming hair fixing polymers" those polymers are understood, which when used in an amount of from 0.1 to 10 percent in an aqueous-alcoholic solution deposit a polymer film on the hair and in this way fix the hair.

Suitable nonionic polymers can be used as ingredient B of the hair treatment composition according to the invention. For example, those nonionic polymers include homopolymers of vinylpyrrolidones, for example those which are sold under the trade name Luviskol® K of BASF, Ludwigshafen, Germany, or PVP-K of ISP, Wayne, N.J., U.S.A., as well as homopolymers of N-vinylformamides, such as those sold under the trade name PVF of National Starch, U.S.A. Additional suitable synthetic film-forming nonionic hair fixing polymers, for example, include copolymerizates of vinylpyrrolidone and vinyl acetate, for example those which are marketed under the trade name LUVISKOL® VA of BASF, Ludwigshafen, Germany; terpolymers of vinylpyrrolidone, vinyl acetate and vinyl propionate, which, for example, are sold under the trade name of LUVISKOL® VAP of BASF, Ludwigshafen, Germany; polyacrylamides, which, for example, are sold under the trade name AKYPOMINE® P 191 of CHEM-Y, Emmerich, Germany or SEPIGEL® 305 of SEPPIC, USA; polyvinyl alcohols, which, for example, are marketed under the trade name ELVANOL® of DuPont or VINOL® 523/540 of Air Products, U.S.A., as well as polyethylene glycols with a molecular weight of 800 to 20,000 g/mol, which, for example, are sold under the trade name LIPOXOL® 1000 of HÜLS AG, Germany, PLURACOL E 4000 of BASF, Germany or UPIWAX® 20,000 of UPI.

Some synthetic anionic, film-forming hair-fixing polymers are suitable as ingredient B. For example, those synthetic anionic, film-forming polymers include t-butylacrylate/ethylacrylate/methacrylic acid terpolymers, which, for example, are marketed under the trade name Luvimer® 100P of BASF, Ludwigshafen, Germany. Additional suitable synthetic film-forming anionic polymers include, for example, crotonic acid-vinyl acetate copolymers, which for example are marketed in the form of a 60% solution in isopropanol/water under the trademark ARISTOFLEX® of HOECHST, Germany. Additional suitable anionic polymers are, for example, terpolymers made from acrylic acid, ethyl acrylate and N-t-butylacryl amide such as those sold under the trade name ULTRAHOLD 8 and ULTRAHOLD STRONG of BASF, Ludwigshafen, Germany.

Some amphoteric polymers are also suitable as ingredient B. Those amphoteric polymers include terpolymers of octylacrylamide, t-butylaminoethylmethacrylate and two or more monomers comprising acrylic acid, methacrylic acid or their esters, for example, those which are obtainable under the trade names AMPHOMER® 28-4910 and AMPHOMER LV-71 of National Starch, U.S.A.

Some cationic polymers are also suitable as ingredient B of the hair treatment composition according to the invention. Those cationic polymer include polyvinyl-pyrrolidone/dimethylaminoethylmethacrylate polymers, which are marketed, for example, under the tradename Gafquat® 755 N of Gaf Co., New York, U.S.A. Additional suitable cationic polymers are, for example, the copolymers made from polyvinylpyrrolidone and imidazolimine methochloride marketed under the trade name LUVIQUAT® HM 550 of BASF AG, Ludwigshafen, Germany; terpolymers of dimethyldiallyl ammonium chloride, sodium acrylate and acrylamide, which are sold under the trade name Merquat® Plus 3300 of Calgon, Pittsburgh, U.S.A.; the terpolymers made from vinyl pyrrolidone, dimethylaminoethylmethacrylate and vinylcaprolactam sold by ISP, U.S.A. under the trade name Gaffix® VC 713; pyrrolidone/ methacrylamidopropyltrimethyl-ammonium chloride copolymers marketed by Gaf under the tradename Gafquat® HS 100 and diquaternary polydimethyl-siloxanes marketed under the tradename Abil® Quat 3272 by GOLDSCHMIDT, Essen, Germany.

Understandably the composition according to the invention can also include additional conventional cosmetic additive ingredients, such as non-fixing nonionic polymers, for example polyethylene glycols with a molecular weight of 600 g/mol, non-fixing anionic polymers and non-fixing natural polymers and their compositions in an amount of preferably from 0.01 to 50% by weight; perfume oils in an amount of preferably from 0.01 to 5 percent by weight; turbidity-inducing agents, such as ethyleneglycoldistearate, in an amount of preferably from 0.01 to 5 percent by weight; wetting agents or emulsifiers from the classes of anionic, cationic, amphoteric or non-ionic surface-active substances, such as fatty alcohol sulfates, ethoxylated fatty alcohols, fatty acid alkanol amides, for example the esters of hydrogenated castor oil fatty acids in an amount of preferably from 0.1 to 30 percent by weight; further moisturizing agents, dye compounds, light protective compositions, antioxidants, luster-imparting agents and preservative materials in an amount of preferably from 0.01 to 10 percent by weight. Additional suitable additive ingredients include Chinese balsam resin and cellulose derivatives, such as hydroxypropyl celluloses, for example those sold under the trademark NISSO SL® of Lehmann & Voss, Hamburg, Germany.

The compositions according to the invention can be employed in different application forms, for example in aerosol preparations as foam or spray or in other non-aerosol forms which are applied by means of a pump or as "Pump and Spray". The composition according to the invention can also be formulated as a dyeing or care-providing hair treatment composition, such as a dying and fixing composition or a care-providing and fixing composition.

When the composition according to the invention is present in the form of an aerosol hair spray or aerosol hair lacquer, it additionally contains a propellant in an amount of from 15 to 85, preferably from 25 to 75, percent by weight and is filled into a pressurized container. For example, alkanes, particularly lower alkanes such as n-butane, i-butane and propane, or their mixtures with dimethyl ether and also gaseous propellants, such as $N_2$, $N_2O$ and $CO_2$ and their mixtures, can be used as the above-mentioned propellant.

The composition for fixing hair can also be present in the form of a non-aerosol hair spray or a non-aerosol hair lacquer sprayable with the help of a suitable mechanically operated spraying device.

By "mechanical spraying apparatus" those devices are to be understood, which allow spraying of a liquid without use of a propellant. A spray pump or an elastic container provided with a spray valve are each suitable as one of these mechanical spraying apparatus. In operation the cosmetic composition according to the invention is filled under pressure in the elastic container which is stretched as a result of the filling and the composition is dispensed from the container on opening of the spray valve because of contraction of the elastic container.

By "hair treatment" the treatment of human head hair for the purposes of making a hair style, for caring or cleaning of the hair is to be understood.

Furthermore the polymer combination according to the invention allows the making of concentrates, which have a reduced water content and/or solvent content. The concentrates are converted into the ready-to-use hair treatment compositions after transport and, if necessary, storage by addition of the required amount of water and/or solvent.

The composition according to the invention has a reduced amount of volatile organic substances, is easily rinsable from the hair and provides a satisfactory fixing of the hair treated with it.

The following examples should illustrate the subject matter of the invention in more detail, without limiting the claims appended hereinbelow. The shellac used in the examples is pre-neutralized with Borax(Spezialschellack SS B 63 HE-N of Stroever, Germany).

EXAMPLES

Example 1
Comparative Viscosity Measurements of Polymer Solutions with added Shellac Aqueous-ethanolic solutions of pure neutralized shellac, pure t-butylacrylate/ethylacrylate/methacrylic acid terpolymer and a mixture of neutralized shellac and t-butylacrylate/ethylacrylate/methacrylic acid terpolymer were prepared with various amounts of ethanol. The kinematic viscosity of these solutions was measured at 25° C. The viscosity measuring device was an Ubbelohde capillary viscometer (ViscoSystem AVS 500 of Schott, Germany). The results are tabulated in the following Table I.

TABLE I

Viscosity of Aqueous-ethanolic Polymer Solutions at 25° C. in $mm^2.s^{-1}$.

| Example | ETHANOL CONTENT, in % by weight | | |
|---|---|---|---|
| | 30% | 50% | 70% |
| 2% by weight, neutralized shellac | 2.5 | 2.8 | 2.5 |
| 6%, t-butylacrylate/ ethylacrylate/methacrylic acid terpolymer | 17.6 | 18.7 | 14.9 |
| 2% by weight, neutralized shellac + 6%, t-butylacrylate/ ethylacrylate/methacrylic acid terpolymer | 17.2 | 18.0 | 13.5 |
| Viscosity Expected with Additivity | 20.1 | 21.5 | 17.4 |

The results tabulated in Table I showed that no increase, but surprisingly a decrease, in viscosity occurs on addition of the polymer substance, shellac, to the polymer solution.

Example 2
Comparative Viscosity Measurements of Polymer Solutions in which a part of the polymers are replaced with Shellac Aqueous-ethanolic solutions of different polymers as well as solutions in which the polymers were partially replaced with shellac neutralized completely with aminomethylpropanol were prepared. The viscosities were measured with the same conditions as in Example 1. The results are tabulated in Table II.

TABLE II

Viscosity of Aqueous-ethanolic Polymer Solutions at 25° C. in $mm^2.s^{-1}$. Concentrations in % by weight.

| Ethanol | 55 | 55 | 55 | 55 | 55 | 55 | 39 | 39 | 37 |
|---|---|---|---|---|---|---|---|---|---|
| Polymer A[1]) | 6 | 4 | 6 | — | — | — | — | — | — |
| Polymer B[2]) | — | — | — | 6 | 4 | 6 | — | — | — |
| Polymer C[3]) | — | — | — | — | — | — | 12 | 8 | 12 |
| Shellac, neutralized | — | 2 | 2 | — | 2 | 2 | — | 2 | 2 |
| Viscosity, in $mm^2.s^{-1}$ | 18.6 | 11.5 | 17.1 | 25.0 | 14.9 | 22.4 | 8.8 | 6.1 | 8.4 |

[1])Polymer A: t-butylacrylate/ethylacrylate/methacrylic acid terpolymer, neutralized
[2])Polymer B: octylacrylamide/t-butylaminoethyl-ethacrylate/acrylic acid terpolymer, neutralized
[3])Polymer C: vinylpyrrolidone/vinylacetate copolymer.

The experiments show that a definite viscosity reduction effect occurs when a portion of the conventional, hair fixing polymers are replaced by shellac.

Example 3
VOC 55% Hair spray Non-aerosol Stronger Hold

| 1.5 g | vinylpyrrolidone/vinyl acetate copolymer |
|---|---|
| 1.0 g | shellac |
| 0.2 g | perfume |
| 55.0 g | ethanol |
| 42.3 g | water |
| 100.0 g | |

Example 4
VOC 55% Hair Spray Non-aerosol Stronger Hold

| 6.0 g | octylacrylamide/t-butylaminoethyl-methacrylate/acrylic acid terpolymer |
|---|---|
| 2.0 g | shellac |
| 1.3 g | 2-aminobutanol |
| 0.2 g | perfume |
| 55.0 g | ethanol |
| 35.5 g | water |
| 100.0 g | |

Example 5
VOC 55% Hair Spray Non-aerosol Normal Hold

| 3.0 g | t-butylacrylate/ethylacrylate/methacrylic acid terpolymer |
|---|---|
| 1.5 g | shellac |
| 0.8 g | 2-amino-2-methylpropanol |
| 0.2 g | perfume |
| 20.0 g | ethanol |
| 35.0 g | dimethylether |
| 35.5 g | water |
| 100.0 g | |

Example 6
Liquid Fixing Composition

| 2.0 g | vinylacetate/crotonic acid copolymer |
|---|---|
| 0.5 g | shellac |
| 0.2 g | perfume |
| 55.0 g | ethanol |
| 42.3 g | water |
| 100.0 g | |

Example 7
Liquid Fixing Composition

| 10.0 g | isodecane |
|---|---|
| 2.0 g | vinylacetate/crotonic acid copolymer |
| 1.0 g | shellac |
| 0.3 g | perfume |
| 50.0 g | ethanol |
| 36.7 g | water |
| 100.0 g | |

Example 8
Sprayable Tinting and Fixing Composition

| 2.50 g | vinylpyrrolidone/vinylacetate copolymer |
|---|---|
| 1.00 g | shellac |
| 0.20 g | hydrogenated castor oil, ethoxylated with 45 mol ethylene oxide |
| 0.05 g | Acid Brown 4(C.I. 14 805) |
| 42.50 g | ethanol |
| 53.75 g | water |
| 100.0 g | |

The disclosure in German Patent Application 196 45 909.5 of Nov. 7, 1996 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair treatment composition for fixing hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:
1. An aqueous-alcoholic hair fixing composition comprising
   from 0.1 to 10 percent by weight of shellac, neutralized from 50 to 100%;
   from 0.01 to 20 percent by weight of at least one film-forming hair fixing synthetic polymer;
   from 10 to 80 percent by weight of at least one alcohol containing from 1 to 4 carbon atoms;

from 20 to 90 percent by weight water; and from 15 to 85% by weight of a propellant;

wherein said at least one film-forming hair fixing synthetic polymer is selected from the group consisting of polyvinyl pyrrolidones, poly-N-vinyl-formamides, vinyl pyrrolidone/vinyl acetate copolymers, vinyl pyrrolidone/vinyl acetate/vinyl propionate terpolymers, polyacrylamides, polyvinyl alcohols, polyethylene glycols with a molecular weight of from 800 to 20,000 g/mol, t-butyl-acrylate/ethylacrylate/methacrylic acid terpolymers, crotonic acid/vinyl acetate copolymers, acrylic acid/ethylacrylate/N-t-butylacrylamide terpolymers, quaternized vinyl pyrrolidone/dimethylaminoethylmethacrylate copolymers, vinyl pyrrolidone/imidazolimine methochloride copolymers, dimethyldiallyl ammonium chloride/sodium acrylate/acrylamide copolymers, vinyl pyrrolidone/dimethyl-aminoethyl-methacrylate/vinyl caprolactam terpolymers, vinyl pyrrolidone/methacrylamidopropyltrimethyl ammonium chloride copolymers, octylacrylamide/t-butylaminoethyl-methacrylate/acrylic acid terpolymers, octylacrylamide/t-butylaminoethylmethacrylate/acrylic acid ester terpolymers, octylacrylamide/t-butylaminoethylmethacrylate/methacrylic acid terpolymers, octylacrylamide/t-butylaminoethyl-methacrylate/methacrylic acid ester terpolymers and quaternized polydimethylsiloxanes.

2. The composition as defined in claim 1, wherein said shellac neutralized from 50 to 100% was made by neutralizing unneutralized shellac with a neutralizing agent selected from the group consisting of primary amines, secondary amines, tertiary amines, aminoalcohols, alkali hydroxides and aqueous ammonia solutions.

3. The composition as defined in claim 1, containing from 30 to 70 percent by weight of said at least one alcohol.

4. The composition as defined in claim 1, containing from 30 to 70 percent by weight of said water.

5. The composition as defined in claim 1, wherein said propellant is at least one member selected from the group consisting of dimethyl ether, alkanes, $N_2$, $N_2O$ and $CO_2$.

6. An aqueous-alcoholic non-aersol hair spray composition for application to hair by means of a mechanical spraying device, said hair fixing composition comprising from 0.1 to 10 percent by weight of shellac, neutralized from 50 to 100%;

from 0.01 to 20 percent by weight of at least one film-forming hair fixing synthetic polymer;

from 10 to 80 percent by weight of at least one alcohol containing from 1 to 4 carbon atoms; and from 20 to 90 percent by weight water;

wherein said at least one film-forming hair fixing synthetic polymer is selected from the group consisting of polyvinyl pyrrolidones, poly-N-vinyl formamides, vinyl pyrrolidone/vinyl acetate copolymers, vinyl pyrrolidone/vinyl acetate/vinyl propionate terpolymers, polyacrylamides, polyvinyl alcohols, polyethylene glycols with a molecular weight of from 800 to 20,000 g/mol, t-butyl-acrylate/ethylacrylate/methacrylic acid terpolymers, crotonic acid/vinyl acetate copolymers, acrylic acid/ethylacrylate/N-t-butylacrylamide terpolymers, quaternized vinyl pyrrolidone/dimethylaminoethylmethacrylate copolymers, vinyl pyrrolidone/imidazolimine methochloride copolymers, dimethyl-diallyl ammonium chloride/sodium acrylate/acrylamide copolymers, vinyl pyrrolidone/dimethylaminoethylmethacrylate/vinyl caprolactam terpolymers, vinyl pyrrolidone/methacrylamidopropyltrimethyl ammonium chloride copolymers, octylacrylamide/t-butylaminoethyl-methacrylate/acrylic acid terpolymers, octylacrylamide/t-butylaminoethylmethacrylate/acrylic acid ester terpolymer, octylacrylamide/t-butylaminoethylmethacrylate/methacrylic acid terpolymers, octylacrylamide/t-butylaminoethyl-methacrylate/methacrylic acid ester terpolymers and quaternized polydimethylsiloxanes.

7. The composition as defined in claim 6, wherein said shellac neutralized from 50 to 100% was made by neutralizing unneutralized shellac with a neutralizing agent selected from the group consisting of primary amines, secondary amines, tertiary amines, aminoalcohols, alkali hydroxides and aqueous ammonia solutions.

8. The composition as defined in claim 6, wherein said composition contains from 30 to 70 percent by weight of said at least one alcohol.

9. The composition as defined in claim 6, wherein said composition contains from 30 to 70 percent by weight of said water.

* * * * *